(12) United States Patent
Curiel

(10) Patent No.: US 6,649,637 B2
(45) Date of Patent: Nov. 18, 2003

(54) INHIBITION OF INTRACELLULAR REPLICATION BY PYRIDINYLIMIDAZOLES

(76) Inventor: Tyler Curiel, 1820 Jefferson Ave., Apt. 2, New Orleans, LA (US) 70115

( * ) Notice: Subject to any disclaimer, the term of this patent is extended or adjusted under 35 U.S.C. 154(b) by 0 days.

(21) Appl. No.: 10/099,084

(22) Filed: Mar. 15, 2002

(65) Prior Publication Data

US 2002/0132843 A1 Sep. 19, 2002

Related U.S. Application Data

(60) Provisional application No. 60/276,678, filed on Mar. 16, 2001, now abandoned.

(51) Int. Cl.$^7$ .................. A61K 31/44; A61K 31/415
(52) U.S. Cl. .......................... 514/341; 514/401
(58) Field of Search ................... 514/341, 401

(56) References Cited

U.S. PATENT DOCUMENTS 4,510,151 A * 4/1985 Lee ........................ 514/341

OTHER PUBLICATIONS

Windholz et al., The Merck Index, Tenth Edition (1983) p. 1152, abstract No. 7884.*

Abdala et al., "Synthesis and antileishmanial activity derived from 2–amino–4,6–dimethylpyridine" Arneimittel–Forschung (2000), 50(5), 479–484 (copy of abstract).*

Wei et al., "Pyridinylimidazole p38 mitogen–activated protein kinase inhibitors block intracellular Toxoplasma gondii replication", International Journal of Parasitology, (2002), 32(8), pp. 969–977. (copy of abstract).*

* cited by examiner

Primary Examiner—Kevin E. Weddington
(74) Attorney, Agent, or Firm—Benjamin Aaron Adler

(57) ABSTRACT

Substituted pyridinylimidazoles SB203580 and SB202190 strongly inhibit replication and cause stage conversion from active tachyzoites to relatively dormant bradyzoites of the medically important, obligate intracellular parasite *Toxoplasma gondii*. The pyridinylimidazoles probably mediate these effects by acting on a presently unidentified homologue(s) of human p38-mitogen activated protein kinase present in the tachyzoites. SB203580 also significantly enhanced in vitro inhibition of *T. gondii* replication by the approved anti-Toxoplasma drug pyrimethamine. The pyridinylimidazoles and related compounds disclosed herein could thus be significant adjuncts to currently available therapies.

17 Claims, 14 Drawing Sheets

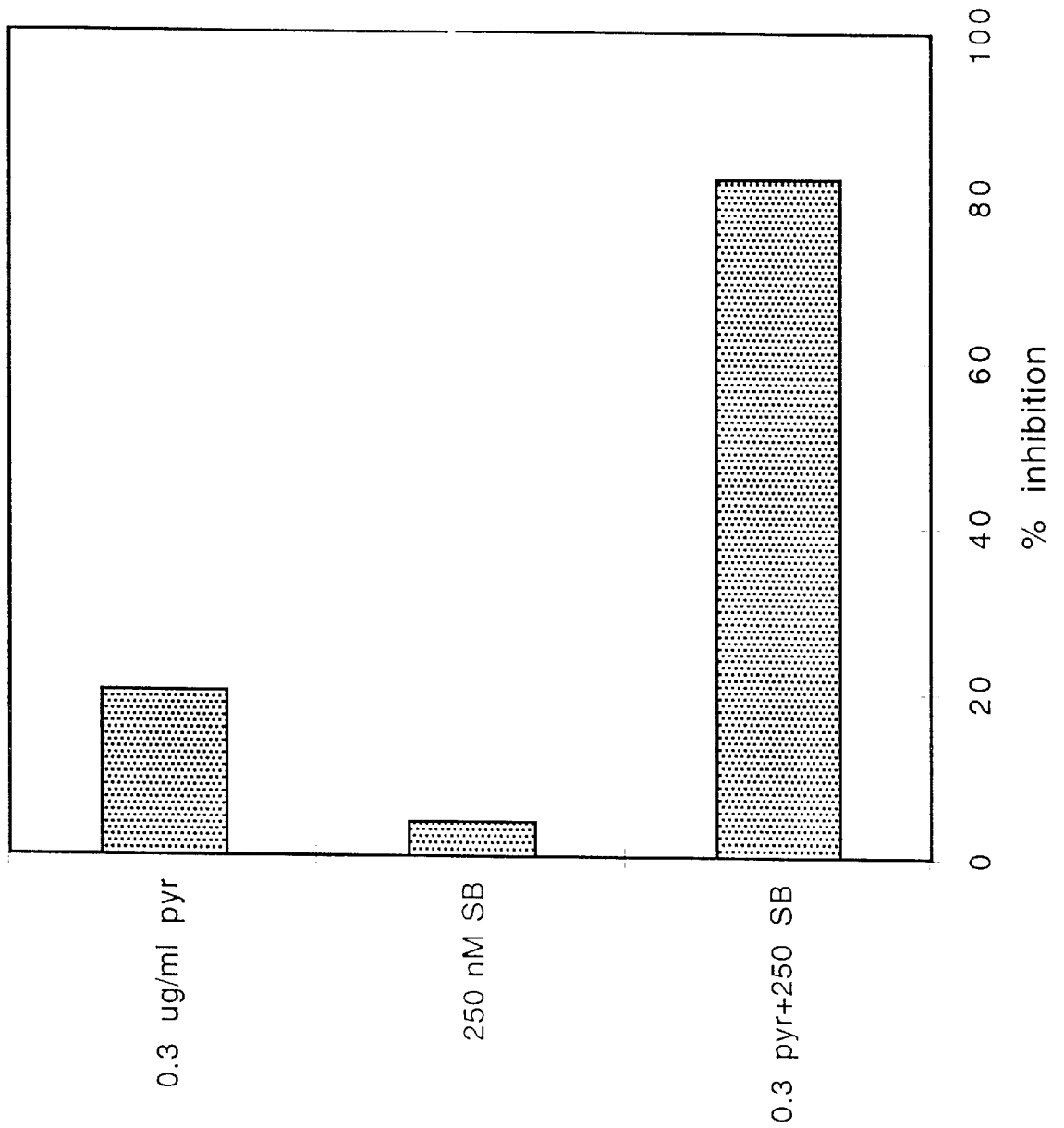

US 6,649,637 B2

INHIBITION OF INTRACELLULAR REPLICATION BY PYRIDINYLIMIDAZOLES

CROSS-REFERENCE TO RELATED APPLICATION

This non-provisional patent application claims benefit of provisional patent application U.S. Serial No. 60/276,678, filed Mar. 16, 2001, now abandoned.

BACKGROUND OF THE INVENTION

1. Field of the Invention

The present invention relates generally to the field of molecular pharmacology of antiparasitics. More specifically, the present invention relates to inhibition of *Toxoplasma gondii* replication by pyridinylimidazoles.

2. Description of the Related Art

Infection with intracellular parasites such as Plasmodium species (agents of malaria), Leishmania species and *Toxoplasma gondii* are a major cause of morbidity and death worldwide. These parasites undergo complex life cycles that require replication within host cells and stage differentiation. Stage differentiation is the conversion from one life form to another. For example, *T. gondii* resides in a dormant tissue cyst form as a relatively metabolically inactive bradyzoite, but quickly reverts to a motile, destructive tachyzoite when specific external signals are sensed. Tachyzoites and bradyzoites are morphologically distinct and express gene products unique to their stage. However, host cell and parasite factors regulating intracellular replication and controlling stage differentiation are poorly understood.

Mitogen activated protein kinases (MAPKs) mediate enzymatic cascades that play diverse roles in mammalian cells including regulation of growth and differentiation, responses to inflammatory stimuli and control of apoptosis. They are highly conserved in evolution and are encoded by all eukaryotes. There are three major families of mitogen activated protein kinases: c-Jun-activated kinases (JNKs), extracellular signal-related kinases (ERKs) and p38s (1, 2).

Mitogen activated protein kinases are activated in a stereotypic fashion. A MAPK kinase (MKKK) is initially activated, which activates a specific MKK or MEK, which in turn activates the individual mitogen activated protein kinase. More than one MKK/MEK may activate a specific mitogen activated protein kinase, and one MKK/MEK may activate members of more than one mitogen activated protein kinase pathway. p38 MAPK is activated by cell stressors such as osmotic shock, heat and infection. p38 MAPK regulates proinflammatory cytokine and IL-10 secretion, apoptosis, proliferation and differentiation (3). Inhibition of p38 MAPK by potent, specific drugs is a novel method to inhibit inflammation in humans in vivo without inducing significant immunosuppression (4).

Pathogens have subverted mitogen activated protein kinase signaling to their own ends. For example, YopJ of *Yersinia enterocolitica* inhibits host cell p38 MAPK activation and interferes with host cell intracellular signaling upon invasion (5, 6). *T. gondii* infection induces host cell p38 MAPK activation (7). Inactivation of host cell mitogen activated protein kinase inhibits parasite entry (7), whereas bombesin and phorbol myristate acetate activate p38 MAPK and increase *T. gondii* infectivity (8). *Listeria monocytogenes* requires activated p42/44 MAPK for cell invasion (9). *Leishmania donovani* promastigotes fail to activate ERK, JNK or p38 following infection of macrophages (10), yet genetic deletion of an endogenous mitogen activated protein kinase in Leishmania demonstrates that it is required for intracellular replication (11). These studies underscore the importance of mitogen activated protein kinase signaling in pathogen infection, host anti-pathogen immunity, and pathogen differentiation and signaling.

Roisin et al. showed for the first time that the medically important, obligate intracellular parasite *Toxoplasma gondii* encodes homologues of human ERK-1 and ERK-2 (12). However, Roisin et al. failed to provide convincing evidence for a role of mitogen activated protein kinase in intracellular replication. Inhibition of *T. gondii* ERK using the specific drug PD098059 (13) slightly reduced intracellular replication that may have been due to defective cell entry, whereas the tyrosine kinase inhibitor genistein had no significant effect on replication (12).

*T. gondii* is a protozoan parasite in the order Coccidia. Cats are the only definitive hosts (14–16). Viable organisms may remain encysted within the host for extended periods of time, and possibly for life (17). With defective cell-mediated immunity, latent infection may recrudesce, producing encephalitis, chorioretinitis, disseminated disease or congenital infection. Populations at risk include recipients of organ allografts or cytotoxic chemotherapy, neonates with perinatally acquired disease, and persons infected with HIV (18–22). Cerebral toxoplasmic encephalitis is an important cause of morbidity and mortality in HIV disease (23–26). Up to 40% of *T. gondii* seropositive, HIV-infected individuals will develop this illness (25).

The mainstay of treatment is combination therapy with pyrimethamine plus sulfadiazine (26). However, treatments are toxic and may interfere with specific antiretroviral therapies in HIV infected individuals. Pyrimethamine is marrow toxic and associated with cytopenias. It also causes rash and is hepatotoxic. Sulfadiazine is also marrow toxic and induces neutropenia. Rash and drug fevers are additional prominent side effects. Marrow toxicity is often dose limiting for both drugs in the setting of advanced HIV disease (27). Neither agent is very active against cysts, and therapy must be given indefinitely in HIV infected individuals (26). Newer agents include Atovaquone and Clindamycin are sometimes substituted for sulfadiazine in the setting of drug related toxicity (27), although none of these agents is very effective. Thus, alternatives or adjuncts allowing for equal efficacy with lower dosing would be of great therapeutic value.

Thus, the prior art is deficient in method and compositions for safely and effectively inhibiting *Toxoplasma gondii* replication in humans. The present invention fulfills this long-standing need and desire in the art.

SUMMARY OF THE INVENTION

*Toxoplasma gondii* is a medically important, obligate intracellular parasite. Little is known regarding factors that regulate its replication within cells. Such knowledge would further understanding of *T. gondii* pathogenesis, and might lead to novel therapeutic strategies. Mitogen activated protein kinases (MAPKs) govern diverse cellular processes including proliferation and differentiation. The present study shows that treatment of *T. gondii* infected cells with SB203580 and SB202190, substituted pyridinylimidazoles that are potent inhibitors of human p38 MAPK, inhibits intracellular *T. gondii* replication. *Toxoplasma gondii* encodes two known functional mitogen activated protein kinase homologues related to human ERK-1 and ERK-2. However, neither the specific ERK inhibitor U0126 nor other general kinase inhibitors affected intracellular *T. gon-*

*dii* replication. Pyridinylimidazole-treated tachyzoites downregulated tachyzoite specific SAG2, upregulated bradyzoite specific p21 and p36, and formed cyst-like structures, suggesting stage conversion from active tachyzoites to relatively dormant bradyzoites. SB203580 also significantly enhanced in vitro inhibition of *T. gondii* replication by the approved anti-Toxoplasma drug pyrimethamine.

Several independent experimental approaches suggest that the antiproliferative effects of pyridinylimidazoles depend on direct action on tachyzoites, not the host cell. Selective inhibition of host p38 MAPK using recombinant adenoviruses had little effect on tachyzoite replication. Pyridinylimidazole-treated tachyzoites developed abnormal morphology suggesting defective parasite division and pyridinylimidazole-resistant mutant tachyzoites were developed through culture in progressively higher drug concentrations. *T. gondii* encodes no known p38 MAPK homologue, but its genome is incompletely characterized. It is proposed that pyridinylimidazoles target a human p38 MAPK homologue in tachyzoites that regulates their replication. As all eukaryotic pathogens, including agents of malaria, Leishmaniasis and Trypanosomiasis encode endogenous mitogen activated protein kinases, drugs inhibiting endogenous mitogen activated protein kinase activation may represent a novel, potentially broadly-acting class of antiparasitic agents. Pyridinylimidazoles also represent tools to elucidate factors governing intracellular tachyzoite replication.

In one aspect of the present invention, there are provided methods of inhibiting intracellular replication of a parasite that possesses endogenous mitogen activated protein kinases. The methods involve treating infected cells with a halogenated imidazole drug that specifically inhibit a human p38 mitogen activated protein kinase homologue expressed in the parasite, or treating infected cells with substituted pyridinylimidazole such as SB203580 or SB202190. In general, the parasite can be a species of Plasmodium, Leishmania or Toxoplasma.

In another aspect of the present invention, there is provided a method of inhibiting intracellular replication of parasite that possesses endogenous mitogen activated protein kinases by treating infected cells with a halogenated imidazole drug that specifically inhibits mitogen activated protein kinases endogenous to said parasite. In general, the parasite can be a species of Plasmodium, Leishmania or Toxoplasma.

In yet another aspect of the present invention, there is provided a method of inhibiting intracellular replication of *Toxoplasma gondii* by treating infected cells with substituted pyridinylimidazole agent SB203580 or SB202190.

The present invention is also directed to improved methods of inhibiting intracellular replication of *Toxoplasma gondii* by treating infected cells with an anti-Toxoplasma drug pyrimethamine in combination with a halogenated imidazole drug or with a substituted pyridinylimidazole drug SB203580 or SB202190. The combined treatments are more effective in inhibiting intracellular replication of *Toxoplasma gondii* as compared to treatment with either drug alone.

The present invention also provides methods of treating an individual infected with *Toxoplasma gondii* using anti-Toxoplasma drug pyrimethamine in combination with a halogenated imidazole drug or with a substituted pyridinylimidazole drug SB203580 or SB202190.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows treatment of *T. gondii* infected fibroblasts with the human p38 MAPK inhibitors SB203580 or SB202190 significantly inhibits tachyzoite replication. Fibroblasts were infected with *T. gondii* tachyzoites at a multiplicity of infection (MOI)=10. Drugs were added 6 hours later after unpenetrated tachyzoites had been washed away, and [$^3$H]methyluracil incorporation was assessed 18 hours later. "Control" is no drug treatment.

FIG. 4 shows tachyzoite cholesterol content and acyl-CoA:cholesterol acyltransferase activity (ACAT) are not significantly altered by SB203580 treatment. Extracellular RH strain tachyzoites were incubated with 10 μM SB203580 for seven hours and assessed for cholesterol content activity and acyl-CoA:cholesterol acyltransferase activity. Tachyzoite viability was not significantly decreased during this extracellular incubation period. The mean of triplicate replications with standard error bars is shown. "Control" is no drug treatment.

FIG. 5 shows SB203580 treatment of infected fibroblasts induces formation of abnormal parasitophorous vacuoles with bi- and multi-nucleated tachyzoites. Fibroblasts were infected with RH strain T. gondii at MOI=10, and 10 μM SB203580 was added 1 hour later. Parasitophorous vacuoles and tachyzoite morphology were assessed by diamidino-2-phenylindole staining 24 hours later using an ultraviolet light with excitation at 410–430 nM.

FIG. 9 shows SB203580 (SB) treatment synergistically enhances the ability of the approved drug pyrimethamine (pyr) to inhibit T. gondii replication in fibroblasts. Fibroblasts were infected overnight and then treated with both drugs simultaneously or individually. Incorporated [$^3$H] methyuracil was measured 48 hours later. Data from one representative experiment is shown.

DETAILED DESCRIPTION OF THE INVENTION

Figure 1A:
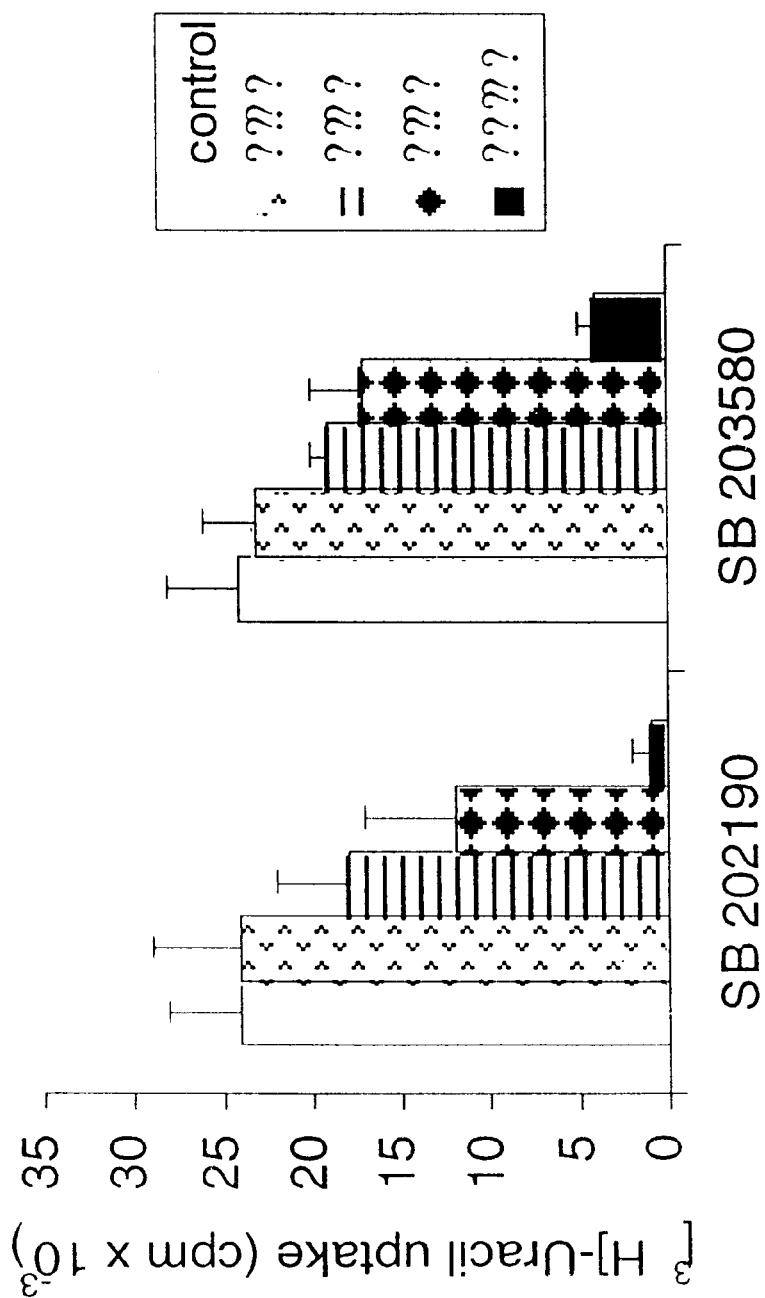
FIG. 1A shows fibroblasts infected with the RH strain of *T. gondii*. Inhibition was significant ($p<0.01$) with 3 $\mu$M SB203580 or SB202190 treatment.

If appearing herein, the following terms shall have the definitions set out below. Any terms or phrases not defined specifically should be interpreted as is customary in modern biochemistry and pharmacology.

As used herein, "substituted pyridinylimdazole drug" refers to the 2,4-substituted 5-pyridinylimidazole compounds SB203580, 4(4-fluorophenyl)-2-(4-methylsulfinylphenyl)-5(4-pyridyl)1H-imidazole, or SB202190, 4-(4-fluorophenyl)-2(4-hydroxphenyl)-5-(4 pyridyl)1H-imidazole, or SB202494, 4-ethyl-2-(4-methoxyphenyl-5(4-pyridyl)1H-imidazole purchased from CalBiochem, La Jolla, Calif. Their derivation, composition and properties are described in detail (Boehm, J. C., J. M. Smietana, M. E. Sorenson, R. S. Garigipati, T. F. Gallagher, P. L. Sheldrake, J. Bradbeer, A. M. Badger, J. T. Laydon, J. C. Lee, L. M. Hillegass, D. E. Griswold. J. Breton, M. C. Chabot-Flatcher, and J. L. Adams. 1966. 1-substituted 4-aryl-5-pyridinylimidazoles: a new class of cytokine suppressive drugs with low 5-lipoxygenase and cyclooxgenase inhibitory potency *J Med Chem* 39:3929–3937.

Although little is known about the role of p38 MAPK in infectious and other processes, recent advances in technology have facilitated study greatly. In particular, there is now a class of substituted pryidinylimidazoles, which specifically inhibit human p38 MAPK (1, 40). The prototypical drugs are SB203580 and SB202190 which are commercially available. The pharmacokinetics, safety and tolerability of SB203580 administration have been established in mice and rats in which this compound has biologic activity against experimental arthritis (4). Similar compounds are currently undergoing human clinical trials as anti-inflammatory agents. The substituted pyridinylimidazole SB202494 is chemically similar yet has no anti-p38 MAPK activity, making it an excellent control.

The present invention shows that the substituted pyridinylimidazoles, such as SB203580 and SB202190, strongly inhibit replication of the medically important intracellular parasite *Toxoplasma gondii*. Specific inhibition of host cell p38 MAPK using recombinant adenoviruses encoding upstream inhibitors blocked host p38 MAPK activation, but had little effect on tachyzoite replication. T. gondii encodes no known p38 MAPK homologue, but its genome is incompletely characterized. T. gondii encodes two known functional MAPK homologues homologous to human ERK-1 and ERK-2. However, neither the specific ERK inhibitor U0126 nor other kinase inhibitors affected intracellular T. gondii replication. Pyridinylimidazole-treated tachyzoites downregulated tachyzoite specific SAG2, upregulated bradyzoite specific p21 and p36, and formed cyst-like structures in treated tissue cultures, suggesting stage conversion from tachyzoites to bradyzoites. As all major pathogens encode endogenous MAPK, drugs targeting them could be effective antiparasitic agents. In this regard, SB203580 significantly enhanced inhibition of T. gondii replication by the approved anti-Toxoplasma drug pyrimethamine.

T. gondii is an opportunistic protozoan parasite causing significant morbidity and mortality in populations with defective cellular immunity including neonates with perinatally acquired disease, recipients of organ allografts or cytotoxic chemotherapy, and persons infected with HIV.

Current treatment for *T. gondii* has a number of limitations. A better understanding of factors governing *T. gondii* replication and stage conversion would further understanding of the pathogenesis of infection.

The present disclosure presents data supporting the concept that an endogenous *T. gondii* p38 MAPK homologue helps regulate intracellular replication and stage conversion from the tachyzoite to the bradyzoite. Because apparently all eukaryotic pathogens express mitogen activated protein kinase homologues, the studies disclosed herein are potentially applicable broadly. Parasite mitogen activated protein kinase pathways represent a heretofore unexploited, potent and broadly applicable target for anti-parasitic drug development. Thus, in addition to being a powerful model for studies of regulation of intracellular parasite growth and differentiation, endogenous mitogen activated protein kinases present targets for therapeutic attack. This concept is strengthened by the fact that related pyridinylimidazole compounds or p38 mitogen activated protein kinase inhibitors are already in human clinical trials for other indications. Thus drug development as anti-parasitic agents could be expedited. Moreover, the pyridinylimidazoles and related compounds disclosed herein could be significant adjuncts to currently available therapies.

SB203580 treatment inhibits host cell p38 MAPK activation, which is associated with reversal of immunosuppression. Treatment with an ERK inhibitor and other kinase inhibitors did not result in reversal of immunosuppression, suggesting specificity of the effects. However, causality is not established for at least 3 reasons: i) the drug may act non-specifically; ii) inhibition of host cell p38 MAPK activation may not be directly related to reversal of immunosuppression; and iii) SB203580 might affect tachyzoites directly. SB203580 does reduce *T. gondii* replication in dendritic cells. As the degree of immunosuppression is directly related to the degree of *T. gondii* replication in dendritic cells, reduced parasite replication may be the direct cause for reversal of immunosuppression, although other factors may also contribute.

The pyridinylimidazole agents evaluated herein do not suppress cellular immunity in mice, although they may inhibit antibody formation slightly (4). These or other similar compounds have been used in human clinical trials with minimal toxicity and no significant induction of immunosuppression (1, 40). Furthermore, immunity against *T. gondii* is mediated primarily by cellular rather than humoral effector mechanisms (28). Proinflammatory cytokines likely play a role in the tissue destruction of acute *T. gondii* infection (45). Thus, inhibition of proinflammatory cytokines through p38 mitogen activated protein kinase inhibition may be therapeutically useful.

SB203580 at concentrations in the p38 MAPK-specific range significantly inhibited intracellular tachyzoite growth, whereas control kinase inhibitors with no mitogen activated protein kinase effects or an inhibitor targeting a non-p38 MAPK (ERK) did not, suggesting non-specific effects were unlikely. Thus, inhibition of intracellular replication appeared to be p38 MAPK-specific. The more slowly growing Me49 strain *T. gondii* tachyzoites were more susceptible to growth inhibition and immunosuppression reversal compared to the more rapidly dividing RH strain. Nonetheless, these data did not distinguish whether a protein in the host cell, the tachyzoite or both, regulated intracellular growth inhibition. A direct effect on tachyzoites was suggested based on the abnormal vacuole and tachyzoite morphology, and on the abnormal alignment of tachyzoites within vacuoles.

Although *T. gondii* encodes no known p38 MAPK homologue, its genome is large and incompletely characterized (46), leaving open the possibility of an unidentified p38 MAPK homologue. Specific inhibition of host cell p38 MAPK using recombinant adenoviruses encoding upstream inhibitors blocked host p38 MAPK activation, but had no effect on tachyzoite replication. As *T. gondii* is sequestered in its parasitophorous vacuole which does not allow proteins greater than 1900 Dalton to pass (47), gene products encoded by these adenoviruses can interfere with host cell, but not parasite protein function. Thus, host cell p38 MAPK may not play a role in control of intracellular *T. gondii* replication, and control of *T. gondii* replication may be regulated by endogenous parasite MAPK, analogous to Leishmania (11).

Incubation of extracellular tachyzoites with pyridinylimidazoles significantly reduced parasite replication, demonstrating a direct effect on tachyzoites independent of any effect of host cell p38 MAPK. Whether this reduced replication is due to reduced host cell entry, reduced intracellular replication or both remains to be determined. The modest decrement in replication effected by control agent and DMSO dimethylsulfoxide (drug diluent) likely represents non-specific toxicity.

Tachyzoites resistant to the antiproliferative effects of SB203580 have been generated. Resistant to blockade from host cell entry by SB203580 may be an independent trait that remains to b e determined. Cross-resistance to SB202190 was observed and expected, as this agent targets the same pathway as SB203580. Development of pyridinylimidazole resistant tachyzoites supports the concept that p38 MAPK-inhibiting agents mediate their effects by targeting tachyzoite rather than host cell proteins.

Upregulation of bradyzoite-specific antigens, and downregulation of tachyzoite-specific antigens suggests that tachyzoite to bradyzoite conversion is induced by these compounds. High pH induces tachyzoite to bradyzoite conversion (48). Dimethylsulfoxide alone did not induce these changes, and drugs did not alter the medium pH, suggesting a specific SB203580-mediated effect. Slow tachyzoite growth is associated with expression of bradyzoite antigens (38). However, pyrimethamine effected significantly lower p36 expression than SB203580, despite almost completely halting replication.

Stage conversion in *T. gondii* is complex and mutlifactorial (38, 49). Stressors such as pH extremes (pH 6.6 or pH 8.0), high temperature (43° C.) (48), and arsenite induce tachyzoite to bradyzoite conversion (32, 38, 48). Immunologic stresses such as interferon-γ treatment (50, 51) or Toxoplasma immune serum (52) also induce bradyzoite formation in vitro. Tachyzoite to bradyzoite conversion also occurs spontaneously in vitro (53), and relates to the speed of parasite replication. Factors that slow tachyzoite replication in vitro such as drugs, anti-parasite cytokines and repeated passaging all increase the expression of bradyzoite-specific antigens (38, 48, 52). Slow growing, less virulent *T. gondii* strains such as Me49 (54) also have an increased tendency for spontaneous bradyzoite conversion (and cyst formation) in vitro (38).

SB203580 induced structures resembling cysts and unusual tachyzoite morphology and arrangement within parasitophorous vacuoles. The induction of bradyzoite-specific antigens and downregulation of tachyzoite-associated antigens strongly suggests that a shift from the rapidly dividing tachyzoite to the bradyzoite is occurring. These events did not appear to be due to stress conditions in culture (in fact, pyridinylimidazoles prevent release of proinflammatory cytokines), or reduced parasite replication. Suboptimal doses of SB203580 or SB202190 in combination with ineffective doses of pyrimethamine cause significant inhibition of intracellular *T. gondii* replication. The inhibition was much higher than that mediated by either agent alone, suggesting a synergistic effect. The combination of agents may thus allow suboptimal drug concentrations to be extremely effective in inhibiting *T. gondii* replication.

A significant drawback to current anti-Toxoplasma therapy is the toxicity of approved agents. If mitogen activated protein kinase inhibition allows lower doses of approved agents to b e equally effective, that represents an additional therapeutic advantage, as toxicity would be reduced. The pyridinylimidazole compounds disclosed herein have the potential to improve efficacy of standard therapies and/or give equal efficacy with lower dosing of standard therapies (and hence fewer side effects).

In one aspect of the present invention, there are provided methods of inhibiting intracellular replication of a parasite that possesses endogenous mitogen activated protein kinases. The methods involve treating infected cells with a substituted pyridinylimidazole drugs such as SB203580 or SB202190 that specifically inhibit a human p38 mitogen activated protein kinase homologue predicted to be expressed in the parasite. In general, the parasite can be a species of Plasmodium, Leishmania or Toxoplasma.

In another aspect of the present invention, there is provided a method of inhibiting intracellular replication of parasite that possesses endogenous mitogen activated protein kinases by treating infected cells with a substituted pyridinylimidazole drug that specifically inhibits mitogen activated protein kinases endogenous to said parasite. In general, the parasite can be a species of Plasmodium, Leishmania or Toxoplasma.

In yet another aspect of the present invention, there is provided a method of inhibiting intracellular replication of *Toxoplasma gondii* by treating infected cells with substituted pyridinylimidazole agents SB203580 or SB202190.

In yet another aspect of the present invention, there is provided a method of inhibiting replication of a parasite, comprising the step of contacting said parasite with an inhibitor of p38 MAPK activation. In one aspect, representative parasites include *T. gondii*, and agents of malaria and Leishmaniasis.

The present invention is also directed to improved methods of inhibiting intracellular replication of *Toxoplasma gondii* by treating infected cells with an anti-Toxoplasma drug pyrimethamine in combination with a substituted pyridinylimidazole drug such as SB203580 or SB202190. The combined treatments are more effective in inhibiting intracellular replication of *Toxoplasma gondii* as compared to treatment with either drug alone.

The present invention also provides methods of treating an individual infected with *Toxoplasma gondii* using anti-Toxoplasma drug pyrimethamine in combination with a substituted pyridinylimidazole drug such as SB203580 or SB202190.

It is contemplated that pharmaceutical compositions may be prepared using the pyridinylimidazoles of the present invention. In such a case, the pharmaceutical composition comprises substituted pyridinylimidazoles and a pharmaceutically acceptable carrier. The pharmacokinetics, safety and tolerability of SB203580 administration have been established in mice and rats (4), and similar compounds are currently undergoing human clinical trials as anti-inflammatory agents. Hence, a person having ordinary skill in this art would readily be able to determine, without undue experimentation, the appropriate dosages and routes of administration of the active component of the present invention. The composition(s) will normally be administered parenterally, preferably intravenously, or orally but other routes of administration will be used as appropriate. See *Remington's Pharmaceutical Science*, 17th Ed. (1990) Mark Publishing Co., Easton, Pa.; and *Goodman and Gilman's: The Pharmacological Basis of Therapeutics*, 8th Ed (1990) Pergamon Press. When used in vivo for therapy, the active composition(s) of the present invention is administered to the patient or an animal in therapeutically effective amounts, i.e., amounts that eliminate or reduce replication of the intracellular parasite.

The following examples are given for the purpose of illustrating various embodiments of the invention and are not meant to limit the present invention in any fashion.

EXAMPLE 1

SB203580 And SB202190 Inhibit Intracellular *T. gondii* Replication

SB203580 and SB202190 (Calbiochem, La Jolla Calif.) are chemically related substituted pyridinylimidazoles that specifically inhibit human p38 MAPK. SB202474 is an additional, related substituted pyridinylimidazole without significant p38 MAPK inhibitory effects in the concentrations used (4). The specific MEK-1/2/5 inhibitor U0126 (29) (Calbiochem) inhibits activation of human ERK-1 and ERK-2. Wortmannin (Sigma) is an inhibitor of phosphoinositol 3-kinase (30). Vanadate has pleiotropic effects on numerous kinases and phosphatases. Stock agents were reconstituted in dimethylsulfoxide (Sigma) at 1 mM and diluted in tissue culture medium immediately prior to use. Cells were infected with *T. gondii* 6 hours prior to addition of drugs which were maintained throughout culture following infection unless otherwise indicated. In long-term cultures, pyridinylimidazoles were completely replaced every 5 days, based on preliminary observations that biologic effects waned after this time. The concentration of drug reducing [$^3$H]methyluracil incorporation into tachyzoites by 50% compared to untreated cultures was defined as the inhibitory concentration (IC$_{50}$), and its value was estimated by linear interpolation of dose response data.

*T. gondii* RH strain was originally obtained from Elmer Pfeffercorn (Dartmouth University, Hanover, N.H.) and Me49 strain was obtained from Randolph Berens and Edward Krug (University of Colo., Denver, Colo.). Tachyzoites were passaged in human foreskin fibroblasts as described (28). Cells were tested periodically for Mycoplasma infection by polymerase chain reaction (Molecular Probes, Eugene, Oreg.) and by staining with Hoescht 33342 dye (Hoescht Chemicals, Frankfurt, Germany) and found to be negative.

Tachyzoites were released from infected fibroblasts by forced passage through a 27-gauge needle, and used within 2 hours of collection to infect new host cells. Tachyzoites were enumerated with a hemacytometer using Trypan blue dye. To evaluate nuclear morphology, infected cells were stained with diamidino-2phenylindole (Sigma) and examined by light microscopy at 400× magnification. To estimate the intensity of *T. gondii* infection, cytospin preparations of aliquots of cells in infected cultures were stained with Giemsa stain and examined by light microscopy using a 40× objective. At least 200 cells per condition were counted.

*T. gondii* tachyzoites metabolize uracil in DNA synthesis, whereas normal human cells do not. Thus, to quantify *T.* gondii tachyzoite replication, 1 μCi [$^3$H]methyluracil (New England Nuclear, Cambridge, Mass.) was added to infected cells in 96 well plastic microtiter plates 16 hours before harvest. Cells were harvested with a Tomtec automated cell harvester (Wallac, Gaithersburg, Md.) and the incorporated radiolabel was analyzed on a Trilux Scintillation counter (Wallac). The mean +/− the standard error of the mean of triplicate determinations is presented.

Addition of SB202190 or SB2035806 hours after infection of fibroblasts significantly inhibited intracellular RH strain T. gondii tachyzoite replication in a dose-dependent fashion measured 16 hours later. There was significant inhibition ($p<0.05$) of intracellular tachyzoite replication by SB202190 at 3 to 5 μM, concentrations of pyridinylimidazoles that are generally accepted to be highly selective for inhibition of p38 MAPK (FIG. 1A). SB203580 also significantly inhibited intracellular T. gondii replication ($p<0.001$), but with a higher $IC_{50}$ (FIG. 1A). Host cell p38 MAPK inhibition reduces the ability of tachyzoites to reinfect cells. However, at this time point, the infected monolayer had not undergone significant lysis as evidenced by light microscopic evaluation.

Figure 1B:
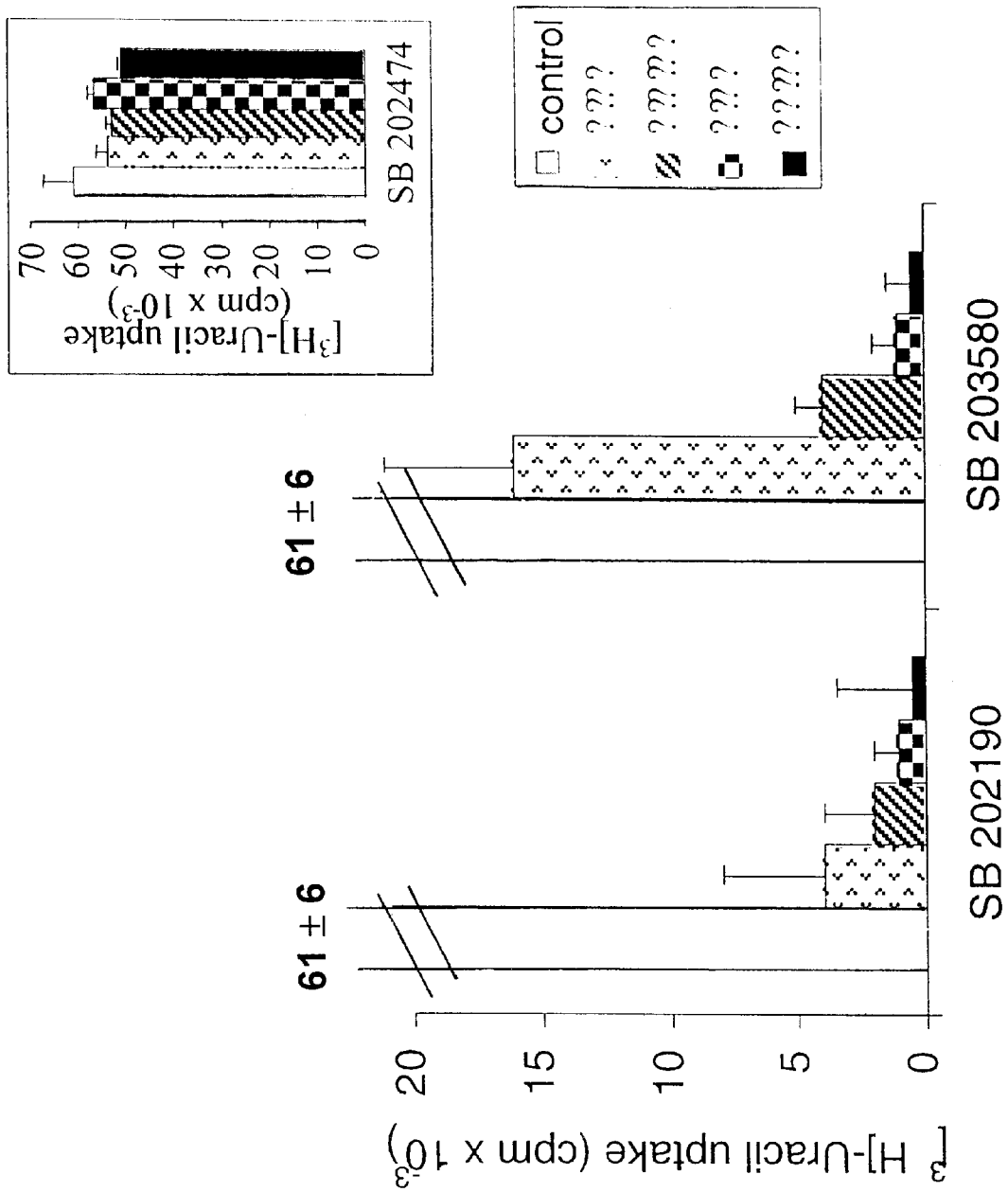
FIG. 1B shows fibroblasts infected with the Me49 strain of *T. gondii*. Inhibition was significant ($p<0.01$) at all concentrations tested. Untreated control counts are off scale, as indicated by the slash marks with the mean counts +/−SEM shown above the bars. The inset shows that treatment of these tachyzoites with SB202474, a related pyridinylimidazole isoform that has no capacity to inhibit human p38 MAPK and has no significant effect on tachyzoite replication.
Figure 1C:
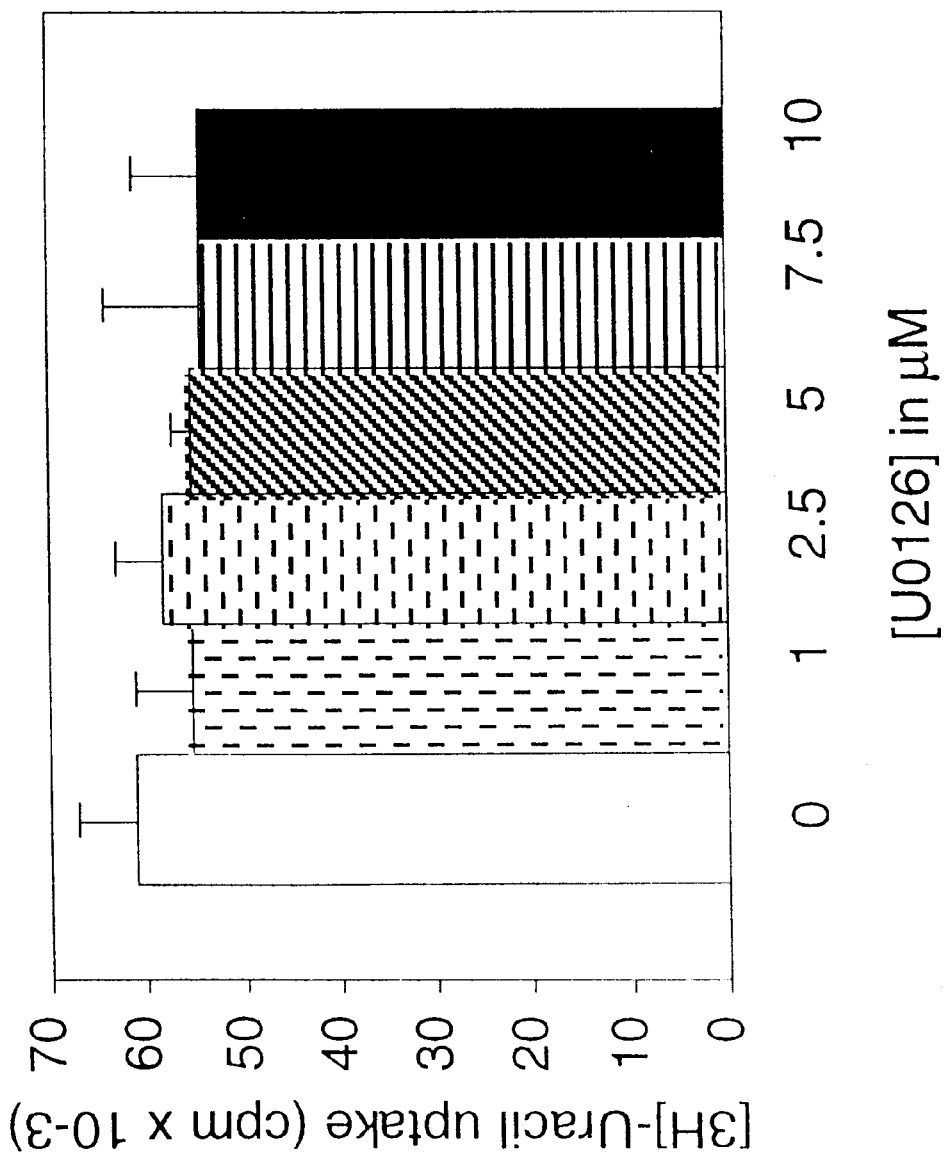
FIG. 1C shows the ERK-1/2 inhibitor U0126 had no significant effect on Me49 tachyzoite replication. Means of triplicate results with standard error bars are shown. One representative experiment of at least 3 with similar results is shown for each panel. Cpm, counts per minute.

T. gondii strain Me49 grows significantly more slowly than RH strain, and is less virulent in mice. The Me49 strain is significantly more susceptible to SB203580 and SB202190 than the RH strain (FIG. 1B). The $IC_{50}$ for SB203580 inhibition of RH strain replication was approximately 6 μM versus 0.5 μM for Me49 ($p<0.01$). The $IC_{50}$ for SB202190 inhibition of RH strain replication was approximately 5 μM vs 0.2 μM for Me49 ($p<0.01$). Thus, the Me49 strain was approximately 12-fold and 25-fold more susceptible to growth inhibition by SB203580 and SB202190 respectively than RH strain as assessed by [$^3$H]methyluracil incorporation. T. gondii encodes functional homologues of the MAPKs ERK-1 and ERK-2. However, treatment with the MEK-1/2/5 inhibitor U0126 at concentrations up to 10-fold higher than those known to inhibit human ERK had no significant effect on Me49 (FIG. 1C) or RH strain (data not shown) T. gondii replication in human fibroblasts.

The preceding experiments do not distinguish whether SB203580 mediates its effects through inhibition of host cell p38 mitogen activated protein kinase, a parasite protein or both. To inhibit host cell p38 MAPK without directly affecting the tachyzoite, fibroblasts were infected with replication defective adenoviruses encoding dominant negative genes for MKK3 or MKK6, the two upstream protein kinases known to activate p38 MAPK (1, 2). Preliminary experiments demonstrated that >95% of fibroblasts were transduced and that gene expression was maximal at 2 to 3 days following recombinant adenovirus infection. Fibroblasts were infected with recombinant adenovirus at a multiplicity of infection of 5000 and infected with T. gondii 24 hours later. Infections were accomplished by removing the medium from confluent fibroblasts, adding the adenovirus in approximately 0.5 cc medium in a 24 well plate, or 50 μl in a 96 well plate for the times indicated.

Figure 2:
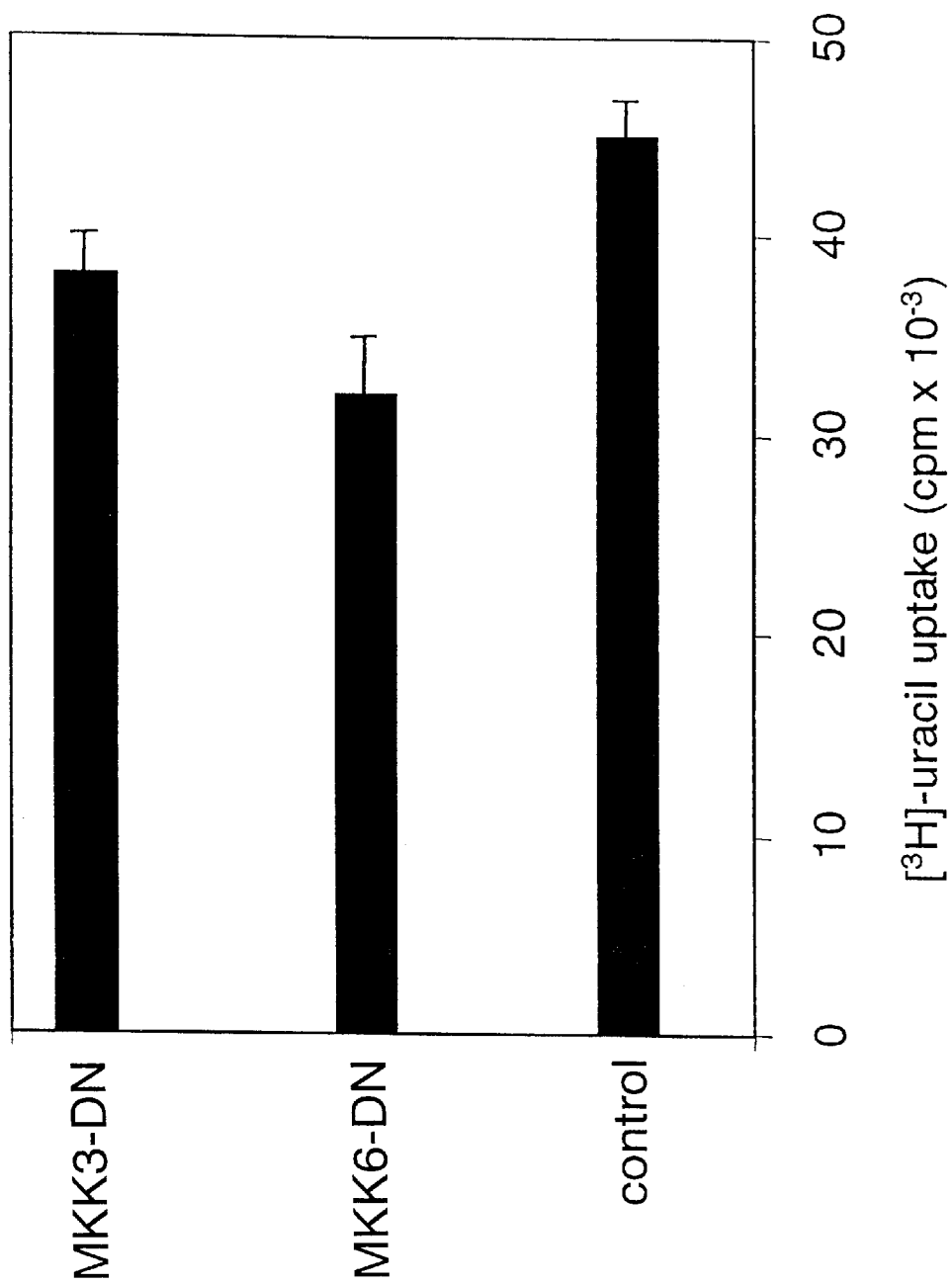
FIG. 2 shows specific inhibition of host p38 MAPK with recombinant adenoviruses expressing dominant negative (DN) MKK3 or MKK6 had minimal effect on intracellular *T. gondii* replication. Fibroblasts were infected with adenoviruses at adenovirus MOI=5000 and infected with RH strain *T. gondii* (MOI=3) 24 hours later. [$^3$H]methyluracil incorporation was assessed 48 hours after *T. gondii* infection. Results are shown as mean±SD. One representative experiment of at least 4 is shown. Similar results were obtained for [$^3$H]methyluracil incorporation assessed at 72 hours after *T. gondii* infection. "Control" is no virus infection. Cpm, counts per minute.

T. gondii tachyzoites replicated normally in host cells infected with adenoviruses encoding dominant negative MKK3 or MKK6, although expression of dominant negative MKK6 effected a slight, but reproducible decrement in tachyzoite replication (FIG. 2). Expression of MKK3 and MKK6 and inhibition of host cell p38 MAPK was confirmed. These vectors inhibit LPS-mediated proinflammatory cytokine production, consistent with their ability to inhibit p38 MAPK (data not shown).

EXAMPLE 2
Incubation of Extracellular Tachyzoites with SB203580 or SB202190 Reduces Intracellular Replication Experiments using dominant negative MKK3 or MKK6 gene products suggested that tachyzoite, not host cell MAPK regulated intracellular replication. To further this concept, extracellular tachyzoites were incubated for 1 hour in SB203580, SB202190, SB202474 or dimethylsulfoxide alone, thoroughly washed and added to fresh fibroblasts in the absence of additional drug or dimethylsulfoxide. 10 μM SB203580 or SB202190 reduced [$^3$H]uracil incorporation approximately 70 to 90% at 48 hours, compared to <15% for SB202474 or dimethylsulfoxide ($p<0.05$).

EXAMPLE 3
Mutant T. gondii Tachyzoites Resistant To SB203580 were Generated

If pyridinylimidazole drugs act directly on tachyzoites, then development of drug-resistant tachyzoites is predictable when parental tachyzoites are grown in progressively increasing drug concentrations. In confirmation, polyclonal cultures of both RH and Me49 tachyzoites resistant to the antiproliferative effects of SB203580 were developed by continual growth in progressively higher drug concentrations over approximately 5 months.

$10^7$ tachyzoites of either RH or Me49 strain were seeded into a T-150 flask onto a confluent monolayer of fibroblasts. After 1 hour, the medium was adjusted to 10 μM SB203580. Fresh drug was added every 5 days, based on the observation that tachyzoite growth increased after this time. Areas of monolayer lysis became apparent after approximately 15 days. By 20 days, sufficient tachyzoites were replicating to allow transfer to a fresh fibroblast monolayer with the drug maintained at 10 μM. Eight days after transfer to a fresh fibroblast monolayer, lysis was again evident, and tachyzoites were again transferred. Now, lysis was evident after 3 days, suggesting that tachyzoite replication in the continued presence of drug was increasing.

Figure 3:
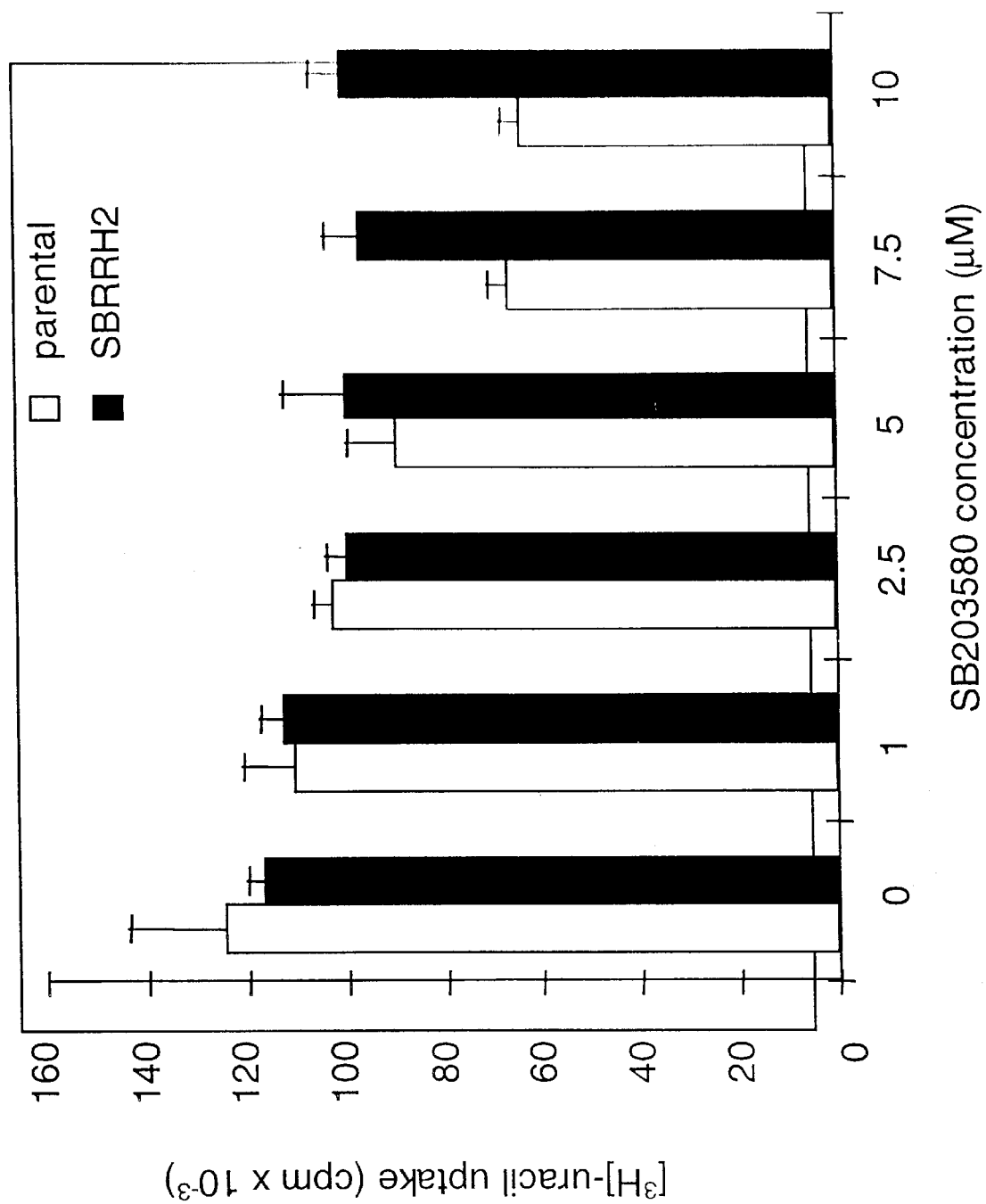
FIG. 3 shows culture of RH tachyzoites in progressively higher SB203580 concentrations demonstrates naturally-occurring mutants significantly more resistant to the antiproliferative effects of SB203580. Four clonal SB203580-resistant tachyzoites were selected by limiting dilution culture. Fibroblasts were infected with mutant tachyzoite SBRRH2 at MOI=10, and SB203580 was added 6 hours later after the extracellular tachyzoites were washed away. [$^3$H]methyluracil incorporation was assessed after 18 h. Mean of triplicate determinations with standard error bars is shown. Cpm, counts per minute.

A polyclonal culture of RH strain tachyzoites was developed that grew as well as parental RH in 10 μM SB203580. Four clonal RH tachyzoites, named SBRRH1 through SBRRH4 were recovered by limiting dilution culture from 768 wells seeded at 0.3 or 1 tachyzoite per well. Clone SBRRH2 was randomly selected for direct comparison to parental of growth inhibition by SB203580. 10 μM SB203580 had no detectable capacity to inhibit replication of SBRRH2 in fibroblasts, whereas this concentration significantly inhibited replication of parental tachyzoites (FIG. 3). The SB203580 $IC_{50}$ for the SB203580-resistant Me49 polyclonal population was approximately 5.5 μM, which is approximately 11-fold higher than that for parental tachyzoites. 11 individual SB203580-resistant Me49 strain clones were produced and selected in parallel cultures, but have not been extensively evaluated. These data strongly suggest that pyridinylimidazoles act on a T. gondii protein. However, a search of the T. gondii EST data base using BLAST software did not detect a homologue of human 38 mitogen activated protein kinase.

EXAMPLE 4
SB203580 Treatment Does Not Affect Tachyzoite Cholesterol Content or Metabolism Mitogen activated protein kinase activation is involved in cholesterol metabolism, and T. gondii requires cholesterol esterification for optimal tachyzoite replication. Therefore, the effects of drug treatment on cholesterol content or metabolism were examined as follows.

Cholesterol esterification activity was assessed by pulse-labeling of cells using radiolabeled fatty acid as substrate.

Briefly, RH *T. gondii* tachyzoites were harvested from fibroblasts, washed in phosphate buffered saline, and aliquots of $10^7$ extracellular parasites were incubated with 10 μM SB203580 or SB202494 for 7 hours. At the time of drug addition, acyl-CoA:cholesterol acyltransferase activity was stimulated with 25-hydroxycholesterol plus cholesterol and cells were pulse-labeled for 2 hours with 20 μl sodium [$^{14}$C]oleate-albumin complex. Lipids were extracted with hexane/isopropanol (3:2 ratio) and the organic solvents evaporated under a nitrogen stream. Lipids were resuspended in chloroform, spotted on TLC silica gel G plates (Fisher, Fairlawn, N.J.) and separated in hexane/ethyl ether/glacial acetic acid (80:20:1 ratio). Cholesterol ester content was determined by liquid scintillation and normalized as pmol $^{14}$C/mg protein. For cytochemical staining of 3-hydroxysterols, fibroblasts were seeded on poly-lysine coated coverslips, infected with RH *T. gondii* tachyzoites and incubated with drugs as described. After 3 days, cells were fixed in paraformaldehyde, rinsed in PBS, stained with filipin (Sigma) and examined by fluorescence microscopy using an excitation filter of 350–410 nm. Cholesterol content was determined in densitometric units measured with an Alpha Imager 2000 (Alpha Innotech Corporation, San Leandro, Calif.).

Figure 4A:
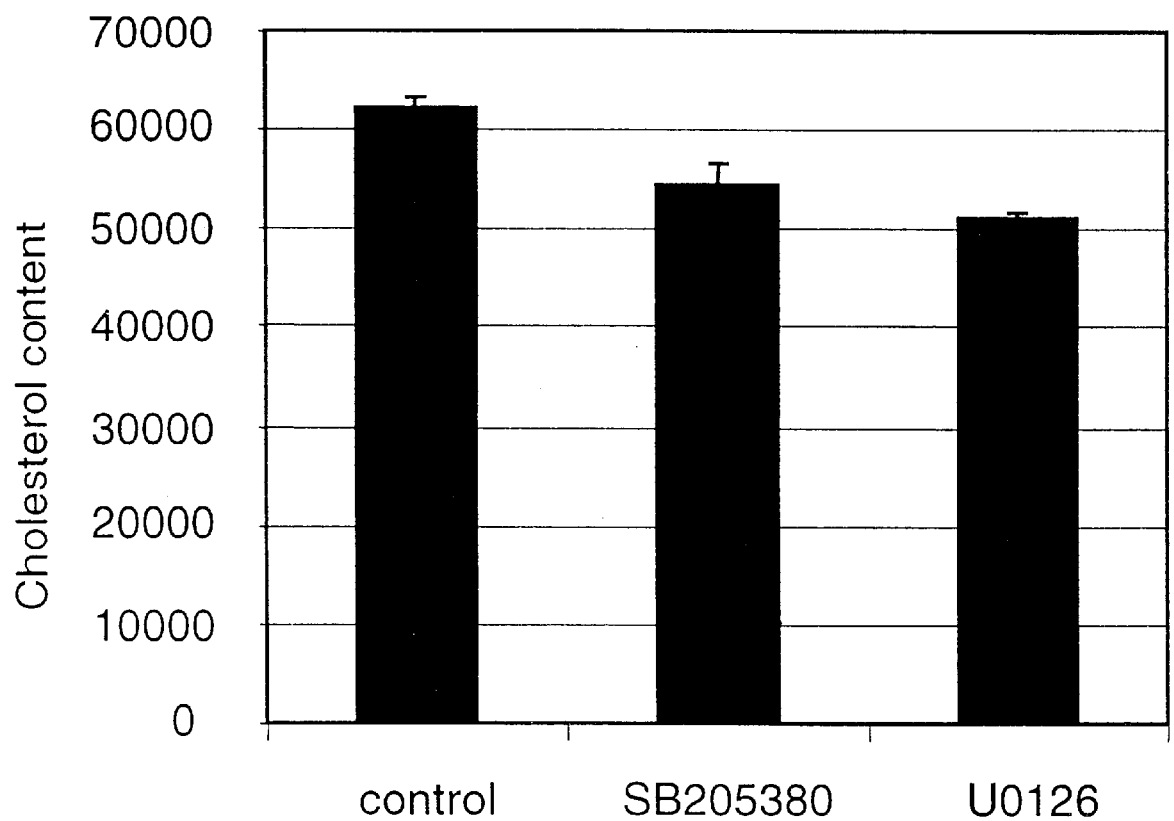
FIG. 4A shows cholesterol content in arbitrary densitometric units.
Figure 4B:
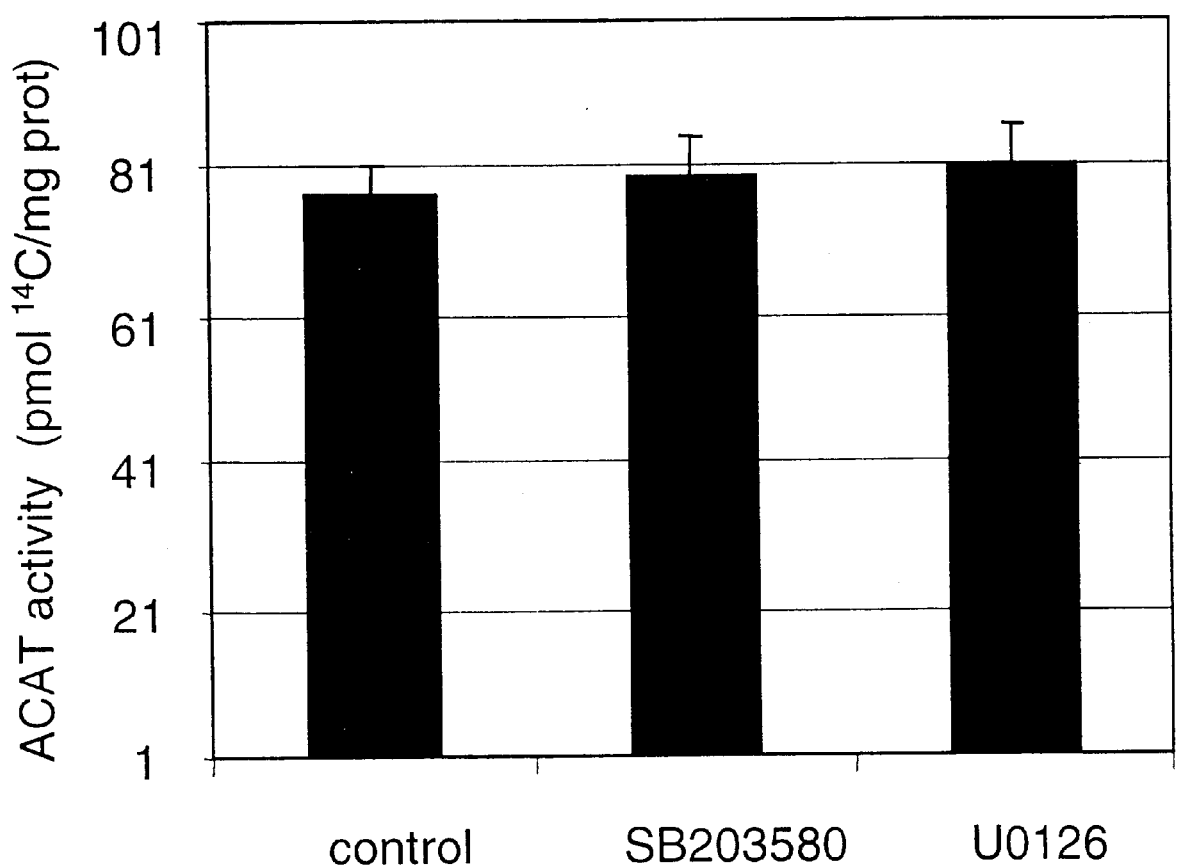
FIG. 4B shows acyl-CoA:cholesterol acyltransferase activity normalized as picomoles of incorporated [$^{14}$C] oleate per mg of total tachyzoite protein (prot) content. One experiment representative of 4 is shown for each measure.

Results shown in FIG. 4 indicated that SB203580 treatment did not interfere with *T. gondii* acyl-CoA:cholesterol acyltransferase activity while it only minimally reduced tachyzoite cholesterol content. Therefore, although *T. gondii* tachyzoites depend on host cell cholesterol and their intrinsic cholesterol metabolic apparatus for optimal replication, pyridinylimidazole p38 MAPK inhibitors do not inhibit tachyzoite replication through reductions in tachyzoite cholesterol content or acyl-CoA:cholesterol acyltransferase activity.

EXAMPLE 5

SB203580 Treatment Induces Abnormal Tachyzoite Morphology

Figure 5A:
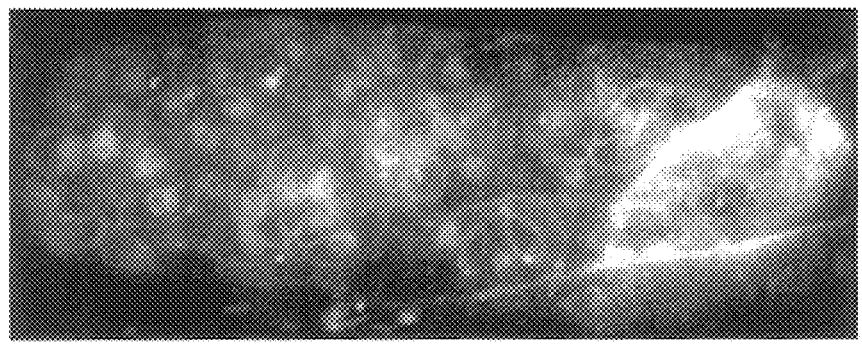
FIG. 5A shows untreated control.
Figure 5B:
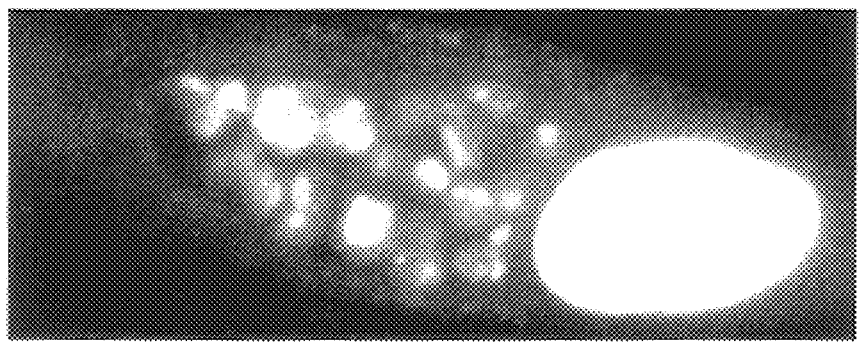
FIG. 5B shows SB203580 treatment.
Figure 5C:
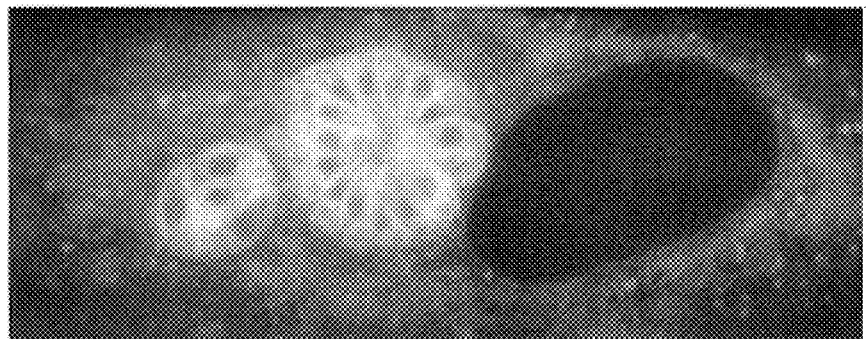
FIG. 5C shows U0126 treated cells at 200× magnification.
Figure 5D:
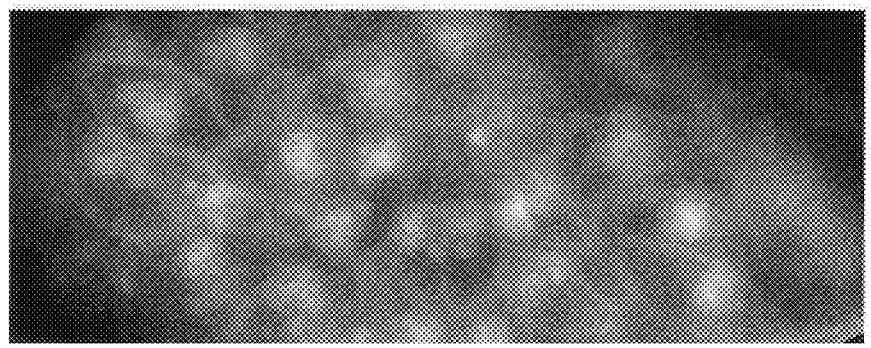
FIG. 5D shows U0126 treated cells at 400× magnification.

Diamidino-2-phenylindole staining of infected cultures treated with SB203580 demonstrated that SB203580 treatment induced formation of tachyzoites with two or more nuclei consistent with incomplete cell division and syncytium formation (FIG. 5B). SB202474 (not shown) and the ERK inhibitor U0126 did not appreciably altered tachyzoite morphology and did not induce binucleated forms (FIGS. 5C and 5D). Tachyzoites growing in the continual presence of SB203580 also developed abnormal vacuole morphology in that the vacuolar space was reduced overall although increased where tachyzoites contacted its edges, and tachyzoites did not align along their long axes as in untreated cultures. SB202474 (not shown) and U0126 treatment did not induce any of these changes in vacuole morphology or tachyzoite arrangement within the vacuoles.

Induction of abnormal tachyzoite and vacuole morphology by pyridinylimidazoles suggests these agents are acting directly on tachyzoites. These effects are reminiscent of effects of p38 mitogen activated protein kinase homologues which regulate cell fission and morphology in the yeast Saccharomyces. Incomplete tachyzoite fission may contribute to the reduced replication mediated by pyridinylimidazoles.

EXAMPLE 6

In vitro Bradyzoite Conversion is Induced

RH infected fibroblasts treated with SB203580 developed cyst-like structures after 3 to 5 days which were not seen in untreated cultures. Ill-formed organisms were visualized within these structures by inverted phase contrast microscopy. These organisms did not exhibit usual rosette formation and were smaller than those formed with normal tachyzoites. The numbers of organisms per vacuole was reduced compared to untreated controls. These features are highly reminiscent of bradyzoites in cell culture (37), suggesting that tachyzoite to bradyzoite conversion w as occurring.

Figure 6A:
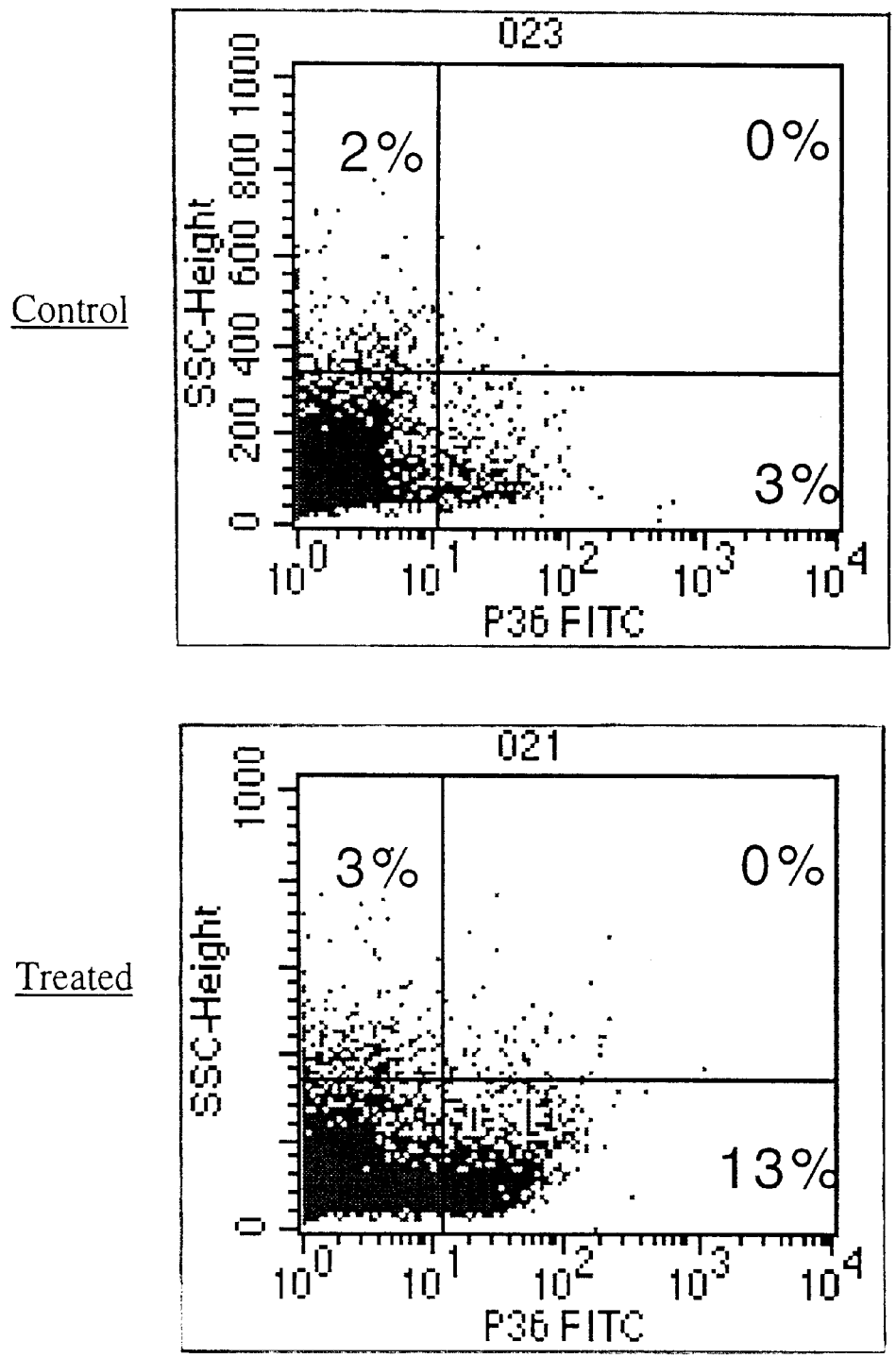
FIG. 6 shows SB203580 and SB202190 treatment affords long-term protection to T. gondii infected cell culture. Fibroblasts were infected with RH strain T. gondii at a MOI of 3 for 2 days, then treated with nothing (FIG. 6A), 10 μM SB203580 (FIG. 6B), 10 μM SB202474 (FIG. 6C) or 10 μM SB202190 (FIG. 6D). Photomicrographs were taken 5 days after treatment was begun. The monolayer is completely destroyed after no treatment or treatment with inactivate control drug SB202474. The SB203580-treated monolayer (FIG. 6B) were approximately 50% destroyed whereas SB202190-treated cells were virtually intact, with little evidence for tachyzoite replication. Note the cyst-like structures (arrows) in SB203580 and SB202190-treated cultures. Original magnification 400×.

Bradyzoites highly express p36 (BSR4), and p21 in cell culture, and downregulate the tachyzoite-specific proteins SAG1 and SAG2 (38, 39). To assess for tachyzoite to bradyzoite stage conversion, fibroblasts were infected with RH strain *T. gondii* and 10 μM SB203580, 5 μM SB202190 or 1 μg pyrimethamine was added 16 hours later. The drugs were replaced every 5 days. After 15 days, adherent, infected fibroblasts were recovered and freed intracellular organisms were analyzed by flow cytometry (FIG. 6A).

Tachyzoites were stained with murine monoclonal antibodies specific for tachyzoite protein (SAG-2, provided by Jacqueline Channon, Dartmouth) or bradyzoite-specific antibodies against p21 or p36 (32) followed by fixation with paraformaldehyde. Flow cytometric data were acquired on a FACS Calibur (Becton-Dickinson, Mountain View, Calif.) and analyzed using CellQuest software (Becton-Dickinson) with 5000 or more events evaluated for each condition. Analysis gates were set using appropriate antibody isotype controls, and dead cells were excluded based on light scatter characteristics.

SB203580 induced a significantly higher number of p36$^+$ organisms than that observed with pyrimethamine ($p<0.05$). However, a clear population of p21$^+$ cells was not evident. After 6 days of culture with SB203580, these organisms also greatly downregulated expression of SAG2 which is a tachyzoite-specific antigen (39) (100% SAG2$^+$ at culture outset vs <15% SAG2$^+$ after 15 days; $p<0.01$).

Figure 6B:
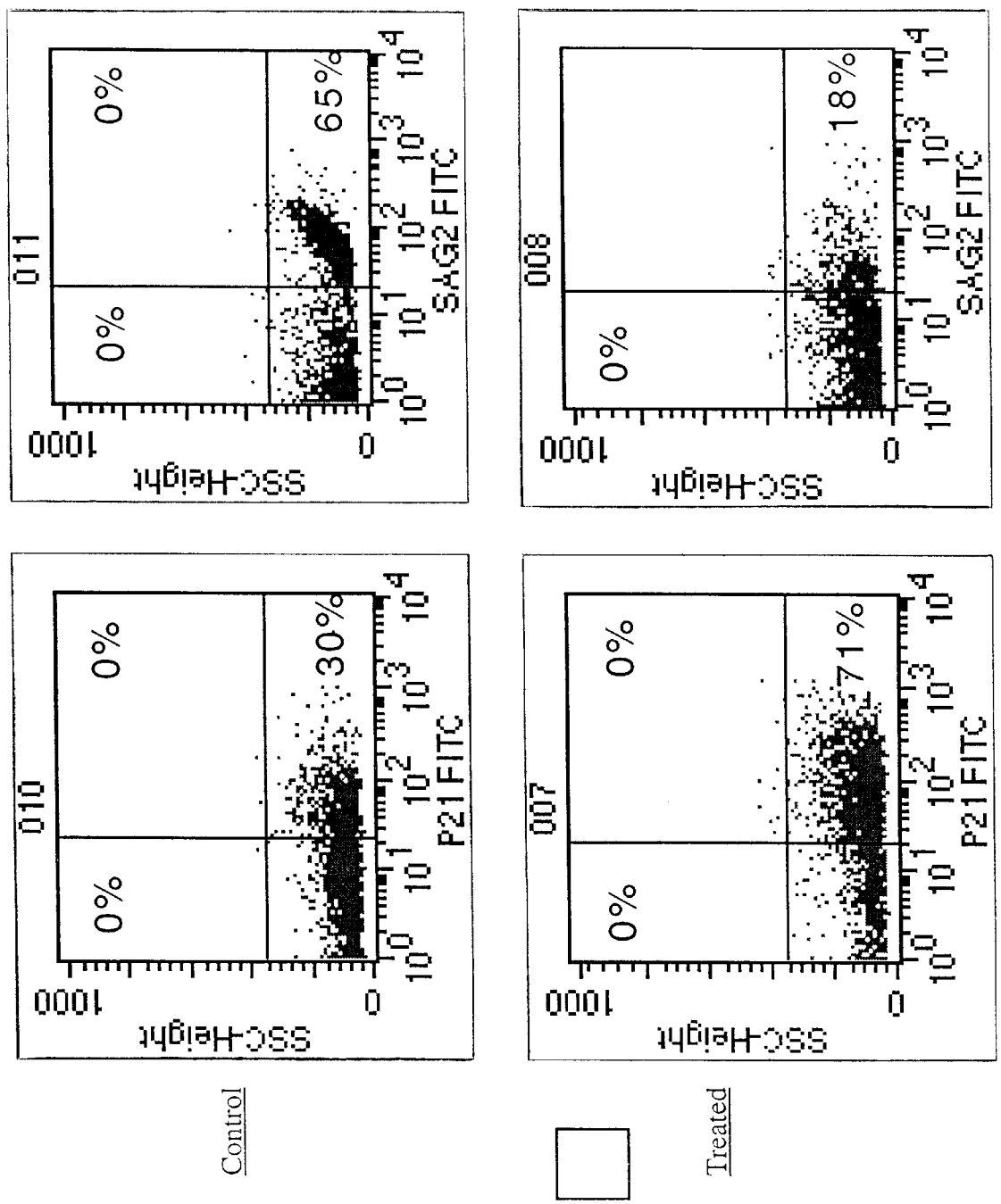

Experiments with Me49 showed similar results. After 5 days of treatment with SB203580, Me49 tachyzoites significantly increased p21 expression and decreased SAG2 expression (FIG. 6B).

EXAMPLE 7

Treatment With SB203580 or SB202190 Protects Fibroblasts From *T. gondii*-Mediated Destruction All experiments thus far were in short term culture. Whether pyridinylimidazoles could limit tissue destruction due to infection of the rapidly growing *T. gondii* strain RH was next determined. Fibroblasts were infected with *T. gondii* at a multiplicity of infection of 3, and then treated with a single dose of 10 μM SB203580, SB202190, SB202474, wortmannin or vanadate 1 hour after infection.

Figure 7A:
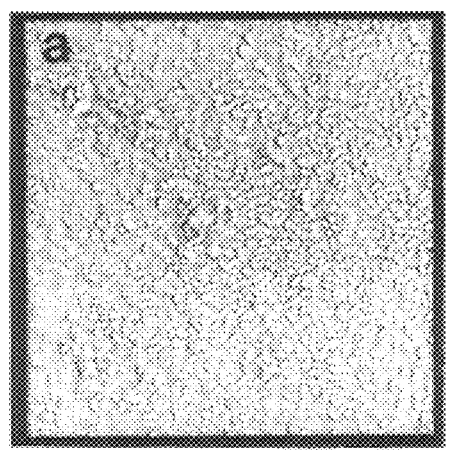
FIG. 7 shows pyridinylimidazole treatment induces stage conversion (tachyzoite to bradyzoite differentiation). Fibroblasts were infected with RH strain tachyzoites and treated with SB203580 starting 6 hours later. After 15 days, residual organisms were released from infected cells and analyzed by flow cytometry. p36 is a bradyzoite-specific marker that was significantly upregulated in treated, but not control cultures (FIG. 7A).
FIG. 7B shows parallel experiment with Me49 strain infected fibroblasts. Bradyzoite-specific p21 was significantly upregulated, whereas tachyzoite-specific SAG2 was downregulated, suggesting stage differentiation after 5 days.
Figure 7B:
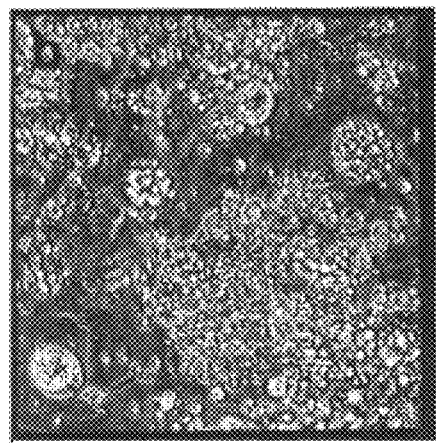

Three days after infection, wortmannin-, vanadate-treated (not shown) and SB202474-treated cultures (FIG. 7C) were essentially destroyed by replication of tachyzoites. SB203580-treated cultures were approximately 50% destroyed (FIG. 7B), whereas SB202190 treated cultures were healthy and confluent with little evidence for intracellular tachyzoite replication (FIG. 7D). By 5 days, all monolayers were completely destroyed except those treated with SB202190. These results paralleled tachyzoite replication over time quantified by [$^3$H]methyluracil incorporation. In additional experiments not shown, infected fibroblast monolayers maintained with constant 10 μM SB203580 were not destroyed even after four weeks, and viable parasite could no longer be recovered up to 3 weeks after drug withdrawal, demonstrating potential for long-term tachyzoite control by pyridinylimidazoles.

EXAMPLE 8
Inhibition of p38 MAPK is Associated with Reversal of *T. gondii* Mediated Immunosuppression Peripheral blood mononuclear cells were obtained by phlebotomy into sterile, heparin-containing glass vials (Becton-Dickinson, Franklin Lakes, N.J.), and purified by Ficoll-Hypaque (Amersham Pharmacia Biotech AB, Sweden) density centrifugation. Cells were adhered to plastic plates (Costar, Corning, N.Y.) for two hours in medium RPMI-1640 (GIBCO BRL, Grand Island, N.Y.) supplemented with heat-inactivated fetal calf serum (GIBCO), 10 mM HEPES buffer, 2 mM L-glutamine and antibiotics. T lymphocytes were purified from PBMC (>98% purity) by depleting CD14, CD19 and CD56-expressing cells using antibody-coated Miltenyi superparamagnetic microbeads (Miltenyi Biotech, Auburn Calif.) according to the manufacturer's directions.

Immature dendritic cells (DC) were produced by growing adherent peripheral blood mononuclear cells in medium containing 100 ng/ml recombinant human granulocyte macrophage-colony stimulating factor (R & D Systems, Minneapolis, Minn.) plus 5 ng/ml recombinant human interleukin-4 (R & D Systems) and used on day 5 to day 7 of culture. Fresh cytokines were replaced in the medium every two or three days. To induce T lymphocyte proliferation, purified CD3$^+$ T lymphocytes were incubated with varying numbers of autologous dendritic cells in 200 RL total volume of medium without exogenous cytokines in triplicate in 96 well round bottomed plastic tissue culture plates. Fifty ng/ml *Staphylococcus aureus* enterotoxin B (Sigma) was added at the start of the culture. To quantitate T lymphocyte proliferation, 1 $\mu$Ci of $^3$H-thymidine (New England Nuclear, Cambridge, Mass.) was added to the microtiter plates (Falcon, Oxnard, Calif.) 16 hours before harvest onto filter mats (Wallac, Gaithersburg, Md.) and analyzed on a Microbeta Trilux liquid scintillation and luminescence counter (Wallac, Turku, Finland). Proliferation assays were performed in triplicate and the mean +/− the standard error of the mean was reported.

Dendritic cells were infected with tachyzoites for 14 to 18 hours at a multiplicity of infection of 10 prior to addition to T lymphocytes. Dendritic cells infected with *T. gondii* tachyzoites did not induce SEB-mediated T cell proliferation, although significant proliferation to SEB by uninfected dendritic cells was observed (FIG. 8).

Figure 8:
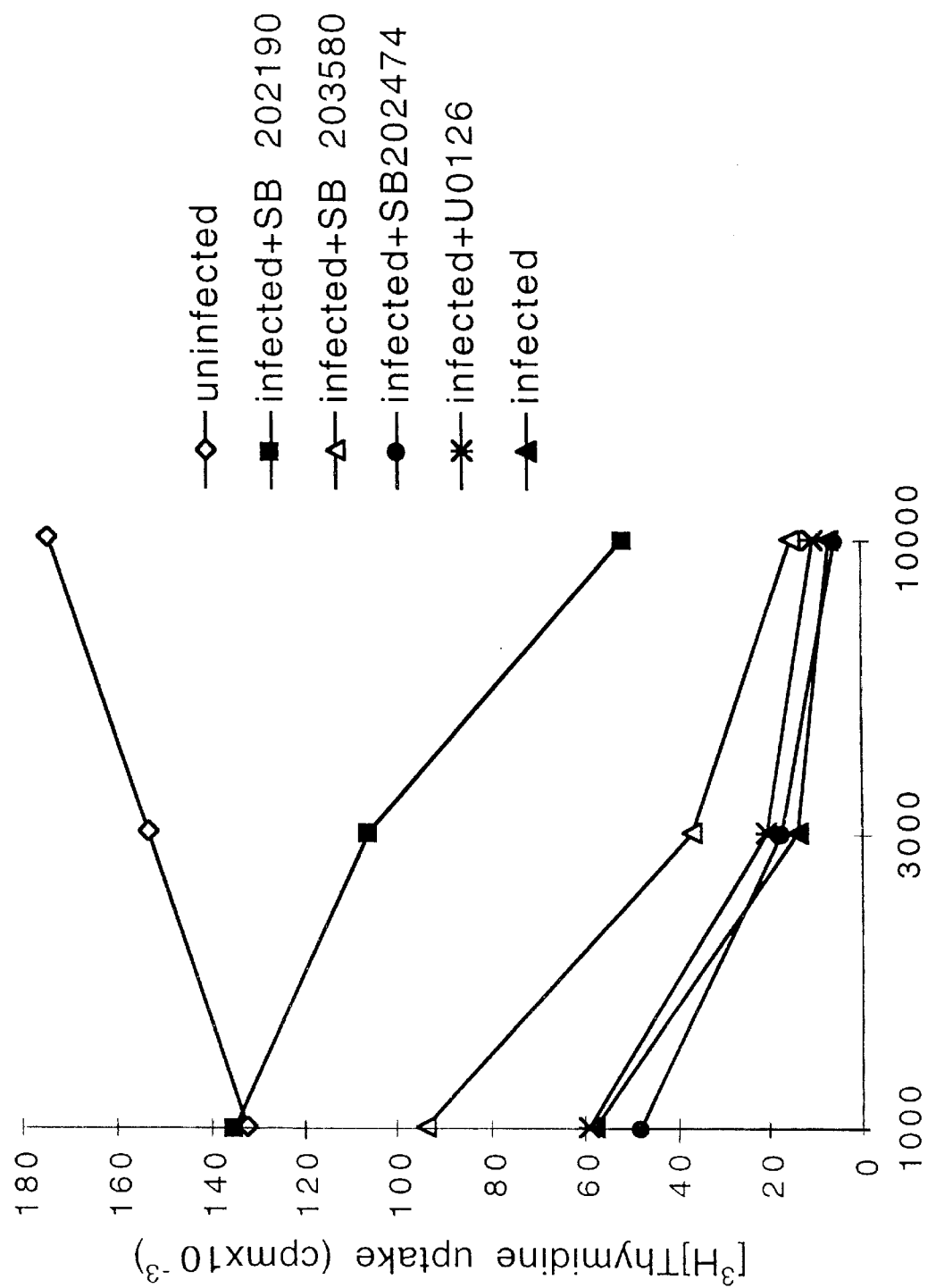
FIG. 8 shows pyridinylimidazole treatment of T. gondii-infected human dendritic cells reverses immunosuppression. Dendritic cells infected with RH strain T. gondii were used to present the superantigen SEB to autologous T cells. Treatment of infected dendritic cells with SB202190 or SB203580 partially reversed the induced immunosuppression. Control pyridinylimidazole SB202474 and the ERK inhibitor U0126 did not reverse immunosuppression. Data from one representative experiment is shown.

Treatment of *T. gondii* infected dendritic cells with SB203580 (p<0.01) or SB202190 (p<0.005) significantly reversed immunosuppression in a dose-dependent fashion, whereas the control compound SB202474 did not (FIG. 8). Neither the specific ENK inhibitor U0126 (13) nor tyrosine kinase or phosphoinositol 3-kinase inhibitors reversed this immunosuppression (data not shown).

EXAMPLE 9
SB203580 Works in Concert with Pyrimethamine to Suppress *T. gondii* Replication Since single-agent therapy for *T. gondii* in humans is not very effective, whether SB203580 or SB202190 could augment the antiparasitic effect of pyrimethamine, an approved agent for treatment of human Toxoplasmosis was tested. Pyrimethamine (Sigma) was dissolved in dimethylsulfoxide and added 1 hour after infection alone or in combination with other agents.

As shown in FIG. 9, 0.3 $\mu$g/ml pyrimethamine does not effectively inhibit tachyzoite replication. As shown above, 1 $\mu$M of SB203580 is an effective dose to inhibit RH *T. gondii* replication. However, 0.25 $\mu$M SB203580 plus suboptimal pyrimethamine (0.3 $\mu$g/ml) significantly decreased [$^3$H] uracil incorporation in RH infected fibroblasts approximately 80%. These data indicate that the pyridinylimidazoles synergistically enhance the ability of the approved drug pyrimethamine to inhibit *T. gondii* replication in fibroblasts. Further synergy analysis can be done using well-accepted methodology (36).

The following references were cited herein:
1. Cobb. 1999. *Prog Biophys Mol Biol* 71:479.
2. Chang and Karin. 2001. *Nature* 410:37.
3. Han et al. 1997. *Nature* 386:296.
4. Boehm et al. 1996. *J Med Chem* 39:3929.
5. Spiik et al. 1999. *Immunol Lett* 68:199.
6. Orth et al. 1999. *Science* 285:1920.
7. Gomez-Marin et al. 1998. *Parasite Immunol* 20:631.
8. Robert-Gangneux et al. 2000. *Parasite* 7:95.
9. Tang et al. 1994. *Mol Biol Cell* 5:455.
10. Prive and Descoteaux. 2000. *Eur J Immunol* 30:2235.
11. Wiese. 1998. *EMBO J* 17:2619.
12. Roisin et al. 2000. *Parasitol Res* 86:588.
13. Duncia et al. 1998. *Bioorg Med Chem Lett* 8:2839.
14. Omata et al. 1996. *Vet Parasitol* 65:173.
15. Lin and Bowman. 1992. *Vet Immunol Immunopathol* 33:69.
16. Kasper. 1989. *Infect Immun* 57:668.
17. Remington and Cavanaugh. 1965. *N Engl J Med* 273:1308.
18. Renold et al. 1992. *Medicine (Baltimore)* 71:224.
19. Porter and Sande. 1992. *N Engl J Med* 327:1643.
20. Carr et al. 1992. *Ann Intern Med* 117:106.
21. Purner et al. 1995. *J Infect Dis* 171:984.
22. Purner et al. 1996. *Infect Immun* 64:4330.
23. Leiva et al. 1998. *J Clin Immunol* 18:283.
24. Albrecht et al. 1995. *Scand J Infect Dis* 27:71.
25. Pueyo et al. 1997. *JAcquir Immune Defic Syndr Hum Retrovirol* 14:459.
26. Luft and Remington. 1992. *Clin Infect Dis* 15:211.
27. Khan et al. 1997. *Antimicrob Agents Chemother* 41:893.
28. Curiel et al. 1993. *J Immunol* 151:2024.
29. Verhagen et al. 2000. *J Exp Med* 192:517.
30. Leu et al. 2000. *Oncogene* 19:1665.
31. Han et al. 2000. *Cell Death Differ* 7:521.
32. Soete et al. 1993. *Exp Parasitol* 76:259.
33. Laemmli. 1970. *Nature* 227:680.
34. Lali et al. 2000. *J Biol Chem* 275:7395.
35. Lee et al. 1999. *Pharmacol Ther* 82:389.
36. Johnson et al. 1991. *J Infect Dis* 164:646.
37. Lane et al. 1996. *Parasitol Res* 82:340.
38. Weiss and Kim. 2000. *Front Biosci* 5:D391.
39. Reichmann et al. 1997. *Parasite Immunol* 19:229.
40. Koprak et al. 1999. *Cell Immunol* 192:87.
41. Egerton et al. 1998. *Int Immunol* 10:223.
42. Foey et al. 1998. *J Immunol* 160:920.
43. Sato et al. 1999. *J Immunol* 162:3865.
44. Song et al. 1999. *J Surg Res* 83:36.
45. Denkers and Gazzinelli. 1998. *Clin Microbiol Rev* 11:569.
46. Ajioka. 1998. *Int J Parasitol* 28:1025.
47. Schwab et al. 1994. *Proc Natl Acad Sci U S A* 91:509.
48. Soete et al. 1994. *Exp Parasitol* 78:361.
49. Dubey et al. 1998. *Clin Microbiol Rev* 11:267.
50. Bohne et al. 1994. *Infect Immun* 62:1761.
51. Weiss et al. 1995. *J Eukaryot Microbiol* 42:150.
52. McHugh et al. 1993. *FEMS Microbiol Lett* 114:325.
53. Bohne et al. 1993. *Infect Immun* 61:1141.
54. Suzuki et al. 1989. *J Immunol* 143:2045.

Any patents or publications mentioned in this specification are indicative of the levels of those skilled in the art to which the invention pertains. Further, these patents and publications are incorporated by reference herein to the same extent as if each individual publication is specifically and individually indicated to b e incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inhibiting intracellular replication of a parasite that possesses endogenous mitogen activated protein kinase activity, comprising the step of:

contacting cells infected with said parasite with a substituted pyridinylimidazole drug that specifically inhibits a human p38 mitogen activated protein kinase homologue expressed in said parasite, wherein said drug inhibits intracellular replication of said parasite in said cells.

2. The method of claim 1, wherein said parasite is selected from the group consisting of Plasmodium, Leishmania and Toxoplasma.

3. The method of claim 1, wherein said substituted pyridinylimidazole drug is SB203580 or SB202190.

4. A method of inhibiting intracellular replication of a parasite that possesses endogenous mitogen activated protein kinase activity, comprising the step of:

contacting cells infected with said parasite with SB203580 or SB202190, wherein said drug inhibits intracellular replication of said parasite in said cells.

5. The method of claim 4, wherein said parasite is selected from the group consisting of Plasmodia, Leishmania and Toxoplasma.

6. A method of inhibiting intracellular replication of a parasite that possesses endogenous mitogen activated protein kinase activity, comprising the step of:

contacting cells infected with said parasite with a substituted pyridinylimidazole drug having at least one halogenated substituent, wherein said drug specifically inhibits mitogen activated protein kinases endogenous to said parasite whereby the intracellular replication of said parasite in said cells is inhibited.

7. The method of claim 6, wherein said parasite is selected from the group consisting of Plasmodium, Leishmania and Toxoplasma.

8. A method of inhibiting intracellular replication of Toxoplasma gondii, comprising the step of:

contacting cells infected with Toxoplasma gondii with SB203580 or SB202190, wherein SB203580 or SB202190 inhibits the intracellular replication of Toxoplasma gondii in said cells.

9. The method of claim 8, wherein treatment with SB203580 or SB202190 causes stage conversion of Toxoplasma gondii from tachyzoites to bradyzoites.

10. A method of inhibiting intracellular replication of Toxoplasma gondii, comprising the step of:

contacting cells infected with Toxoplasma gondii with a combination of an anti-Toxoplasma drug and a substituted pyridinylimidazole drug having at least one halogenated substituent that specifically inhibits a human p38 mitogen activated protein kinase homologue expressed in Toxoplasma gondii, wherein treatment with said drug combination increases inhibition of intracellular Toxoplasma gondii replication in said cells in comparison to treatment with either said anti-Toxoplasma drug or said substituted pyridinylimidazole drug alone.

11. The method of claim 10, wherein said anti-Toxoplasma drug is pyrimethamine.

12. A method of inhibiting intracellular replication of Toxoplasma gondii, comprising the step of:

contacting cells infected with Toxoplasma gondii with a combination of an anti-Toxoplasma drug and one of SB203580 or SB202190, wherein treatment with said drug combination increases inhibition of intracellular Toxoplasma gondii replication in said cells in comparison to treatment with any one of said anti-Toxoplasma drug, SB203580 or SB202190.

13. The method of claim 12, wherein said anti-Toxoplasma drug is pyrimethamine.

14. A method of treating an individual infected with Toxoplasma gondii, comprising the step of:

administering in combination to said individual a pharmacologically effective dose of pyrimethamine and a substituted pyridinylimidazole drug having at least one halogenated substituent that specifically inhibits a human p38 mitogen activated protein kinase homologue expressed in Toxoplasma gondii, wherein treatment with said drug combination inhibits intracellular replication of Toxoplasma gondii in said individual.

15. A method of treating an individual infected with Toxoplasma gondii, comprising the step of:

administering in combination to said individual a pharmacologically effective does of pyrimethamine and one of SB203580 or SB202190, wherein treatment with said drug combination inhibits intracellular replication if Toxoplasma gondii in said individual.

16. A method of inhibiting replication of a parasite, comprising the step of contacting said parasite with an inhibitor of p38 MAPK activation.

17. The method of claim 16, wherein said parasite is selected from the group consisting of T. gondii, and agents of malaria and Leishmaniasis.

* * * * *